(12) United States Patent
Ashby et al.

(10) Patent No.: US 7,875,043 B1
(45) Date of Patent: Jan. 25, 2011

(54) CINCHING LOOP

(75) Inventors: Mark Ashby, Laguna Niguel, CA (US);
Roy D. Bertolet, Ormond Beach, FL
(US); Tin T. Tran, Anaheim, CA (US);
Andrew H. Cragg, Edina, MN (US)

(73) Assignee: Sub-Q, Inc., San Clemente, CA (US)

( * ) Notice: Subject to any disclaimer, the term of this patent is extended or adjusted under 35 U.S.C. 154(b) by 386 days.

(21) Appl. No.: 11/008,748

(22) Filed: Dec. 8, 2004

Related U.S. Application Data

(60) Provisional application No. 60/528,383, filed on Dec. 9, 2003.

(51) Int. Cl.
*A61B 17/04* (2006.01)
(52) U.S. Cl. .......................... 606/148; 606/144; 289/1.2
(58) Field of Classification Search ................. 606/148, 606/139, 144, 145; 289/1.2, 2, 17, 1.5
See application file for complete search history.

(56) References Cited

U.S. PATENT DOCUMENTS

| | | | |
|---|---|---|---|
| 451,094 A | 5/1886 | Morris | |
| 581,235 A | 4/1897 | Kenyon | |
| 1,578,517 A | 3/1926 | Hein | |
| 2,086,580 A | 7/1937 | Shirley | |
| 2,370,319 A | 2/1945 | Lippencott | |
| 2,492,458 A | 12/1946 | Bering, Jr. | |
| 2,465,357 A | 3/1949 | Correll | |
| 2,507,244 A | 5/1950 | Correll | |
| 2,558,395 A | 6/1951 | Studer | |
| 2,597,011 A | 5/1952 | MacMasters et al. | |
| 2,680,442 A | 6/1954 | Linzmayer | |
| 2,761,446 A | 9/1956 | Reed | |
| 2,814,294 A | 11/1957 | Figge | |
| 2,824,092 A | 2/1959 | Thompson | |

(Continued)

FOREIGN PATENT DOCUMENTS

EP        0032826        7/1981

(Continued)

OTHER PUBLICATIONS

Ashley, Clifford. The Ashley Book of Knots. Doubleday: NY, 1944. p. 80.*

(Continued)

*Primary Examiner*—Todd E Manahan
*Assistant Examiner*—Katherine M Dowe
(74) *Attorney, Agent, or Firm*—Seager, Tufte & Wickhem, LLC

(57) ABSTRACT

A solution is provided to release a tissue cinching loop within a body having a first thread having a first end and a second end, and a second thread having a first half having a first tip, a second half having a second tip, a bottom half having a link, and a top half, wherein the first end is inserted through the link. A first knot is formed around the first thread with the top half thereby forming a loop where the diameter of the loop decreases as the knot is pushed into the body and the first thread is pulled out of the body and where the loop is released within the body when the first end is pulled out of the body.

21 Claims, 12 Drawing Sheets

U.S. PATENT DOCUMENTS

| | | |
|---|---|---|
| 2,874,776 A | 2/1959 | Hooe |
| 2,899,362 A | 8/1959 | Sieger, Jr. et al. |
| 2,997,195 A | 8/1961 | Yeun |
| 3,157,524 A | 11/1964 | Artandi |
| 3,358,689 A | 12/1967 | Higgens |
| 3,411,505 A | 11/1968 | Nobis |
| 3,703,174 A | 11/1972 | Smith |
| 3,724,465 A | 4/1973 | Duchane |
| 3,736,939 A | 6/1973 | Taylor |
| 4,000,741 A | 1/1977 | Binard et al. |
| 4,018,229 A * | 4/1977 | Komiya ................. 606/139 |
| 4,098,728 A | 7/1978 | Rosenblatt |
| 4,211,323 A | 7/1980 | Olsen |
| 4,218,155 A | 8/1980 | Weidner |
| 4,219,026 A | 8/1980 | Layton |
| 4,224,945 A | 9/1980 | Cohen |
| 4,238,480 A | 12/1980 | Sawyer |
| 4,292,972 A | 10/1981 | Pawelchak |
| 4,323,072 A | 4/1982 | Rosenbluth et al. |
| 4,340,066 A | 7/1982 | Shah |
| 4,390,018 A | 6/1983 | Zukowski |
| 4,404,970 A | 9/1983 | Sawyer |
| 4,405,314 A | 9/1983 | Copi |
| 4,515,637 A | 5/1985 | Cioca |
| 4,573,576 A | 3/1986 | Krol |
| 4,587,969 A | 5/1986 | Gillis |
| 4,588,395 A | 5/1986 | Lemelson |
| 4,619,261 A | 10/1986 | Guerriero |
| 4,619,913 A | 10/1986 | Luck et al. |
| 4,644,649 A | 2/1987 | Seaman et al. |
| 4,645,488 A | 2/1987 | Matukas |
| 4,699,616 A | 10/1987 | Norwak |
| 4,708,718 A | 11/1987 | Daniels |
| 4,744,364 A | 5/1988 | Kensey |
| 4,790,819 A | 12/1988 | Li et al. |
| 4,829,994 A | 5/1989 | Kurth |
| 4,832,688 A | 5/1989 | Sagae et al. |
| 4,836,204 A | 6/1989 | Landymore et al. |
| 4,839,204 A | 6/1989 | Yoshino |
| 4,850,960 A | 7/1989 | Grayzel |
| 4,852,568 A | 8/1989 | Kensey |
| 4,869,143 A | 9/1989 | Merrick |
| 4,890,612 A | 1/1990 | Kensey |
| 4,900,303 A | 2/1990 | Lemelson |
| 4,929,246 A | 5/1990 | Sinofsky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,049,138 A | 9/1991 | Chevalier et al. |
| 5,053,046 A | 10/1991 | Janese |
| 5,061,274 A | 10/1991 | Kensey |
| 5,080,655 A | 1/1992 | Haaga |
| 5,106,376 A | 4/1992 | Mononen et al. |
| 5,108,421 A | 4/1992 | Fowler |
| 5,129,889 A | 7/1992 | Hahn |
| 5,160,323 A | 11/1992 | Andrew |
| 5,163,904 A | 11/1992 | Lampropoulos et al. |
| 5,167,624 A | 12/1992 | Butler et al. |
| 5,192,290 A | 3/1993 | Hilal |
| 5,192,300 A | 3/1993 | Fowler |
| 5,192,301 A | 3/1993 | Kamiya et al. |
| 5,195,988 A | 3/1993 | Haaga |
| 5,217,470 A * | 6/1993 | Weston ................. 606/148 |
| 5,219,899 A | 6/1993 | Panster et al. |
| 5,220,926 A | 6/1993 | Jones |
| 5,221,259 A | 6/1993 | Weldon et al. |
| 5,232,453 A | 8/1993 | Plass et al. |
| 5,242,683 A | 9/1993 | Klaveness |
| 5,254,105 A | 10/1993 | Haaga |
| 5,275,616 A | 1/1994 | Fowler |
| 5,282,827 A | 2/1994 | Kensey et al. |
| 5,292,309 A | 3/1994 | Van Tassel et al. |
| 5,299,581 A | 4/1994 | Donnell et al. |
| 5,310,407 A | 5/1994 | Casale |
| 5,320,639 A | 6/1994 | Rudnick |
| 5,322,515 A | 6/1994 | Karas et al. |
| 5,325,857 A | 7/1994 | Nabai et al. |
| 5,334,216 A | 8/1994 | Vidal et al. |
| 5,342,388 A | 8/1994 | Toller |
| 5,350,399 A | 9/1994 | Erlebacher et al. |
| 5,352,211 A | 10/1994 | Merskelly |
| 5,366,480 A | 11/1994 | Corriveau et al. |
| 5,370,656 A | 12/1994 | Shevel |
| 5,383,896 A | 1/1995 | Gershony et al. |
| 5,383,899 A | 1/1995 | Hammersiag |
| 5,385,550 A | 1/1995 | Su et al. |
| 5,388,588 A | 2/1995 | Nabai et al. |
| 5,391,183 A | 2/1995 | Janzen et al. |
| 5,399,361 A | 3/1995 | Song et al. |
| 5,405,352 A * | 4/1995 | Weston ................. 606/148 |
| 5,417,699 A | 5/1995 | Klein |
| 5,419,765 A | 5/1995 | Weldon et al. |
| 5,431,639 A | 7/1995 | Shaw |
| 5,437,292 A | 8/1995 | Kipshidze |
| 5,437,631 A | 8/1995 | Janzen |
| 5,443,481 A | 8/1995 | Lee |
| 5,447,502 A | 9/1995 | Haaga |
| 5,458,570 A | 10/1995 | May, Jr. |
| 5,462,194 A | 10/1995 | Barawell |
| 5,467,780 A | 11/1995 | Nabai et al. |
| 5,478,352 A | 12/1995 | Fowler |
| 5,479,936 A | 1/1996 | Nabai et al. |
| 5,486,195 A | 1/1996 | Myers |
| 5,490,736 A | 2/1996 | Haber |
| 5,507,279 A | 4/1996 | Fortune |
| 5,522,840 A | 6/1996 | Krajicek |
| 5,522,850 A | 6/1996 | Yomtov et al. |
| 5,526,822 A | 6/1996 | Burbank et al. |
| 5,527,332 A | 6/1996 | Clement |
| 5,529,577 A | 6/1996 | Hammershiag |
| 5,540,715 A | 7/1996 | Katsaros et al. |
| 5,542,914 A | 8/1996 | Van Iten |
| 5,545,175 A | 8/1996 | Abidin et al. |
| 5,545,178 A | 8/1996 | Kensey et al. |
| 5,554,108 A | 9/1996 | Browning et al. |
| 5,558,853 A | 9/1996 | Quay |
| 5,571,168 A | 11/1996 | Toro |
| 5,591,204 A | 1/1997 | Janzen et al. |
| 5,591,205 A | 1/1997 | Fowler |
| 5,601,207 A | 2/1997 | Paczonay |
| 5,601,601 A | 2/1997 | Tal et al. |
| 5,601,602 A | 2/1997 | Fowler |
| 5,601,603 A | 2/1997 | Illi |
| 5,609,597 A * | 3/1997 | Lehrer ................. 606/139 |
| 5,620,461 A | 4/1997 | Muijs Van De Moer |
| 5,645,566 A | 7/1997 | Brenneman et al. |
| 5,645,849 A | 7/1997 | Pruss et al. |
| 5,649,547 A | 7/1997 | Ritchart et al. |
| 5,653,730 A | 8/1997 | Hammersiag |
| 5,665,107 A | 9/1997 | Hammersiag |
| 5,674,346 A | 10/1997 | Kundel |
| 5,676,689 A | 10/1997 | Kensey |
| 5,681,279 A | 10/1997 | Roper et al. |
| 5,707,393 A | 1/1998 | Kensey et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,775,333 A | 7/1998 | Burbank et al. |
| 5,782,861 A | 7/1998 | Cragg et al. |
| 5,800,389 A | 9/1998 | Burney et al. |
| 5,810,806 A | 9/1998 | Ritchart et al. |
| 5,827,218 A | 10/1998 | Nguyen et al. |

| | | | |
|---|---|---|---|
| 5,830,130 A | 11/1998 | Janzen et al. | |
| 5,858,008 A | 1/1999 | Capaccio | |
| 5,868,762 A | 2/1999 | Cragg et al. | |
| 5,902,310 A | 5/1999 | Foerster et al. | |
| 5,931,165 A | 8/1999 | Reich et al. | |
| 5,931,855 A * | 8/1999 | Buncke | 606/228 |
| 5,984,950 A | 11/1999 | Cragg et al. | |
| 6,007,563 A | 12/1999 | Nash et al. | |
| 6,027,471 A | 2/2000 | Fallon et al. | |
| 6,027,482 A | 2/2000 | Imbert | |
| 6,033,427 A | 3/2000 | Lee | |
| 6,056,768 A | 5/2000 | Cates et al. | |
| 6,063,061 A | 5/2000 | Wallace et al. | |
| 6,066,325 A | 5/2000 | Wallace et al. | |
| 6,071,300 A | 6/2000 | Brenneman et al. | |
| 6,071,301 A | 6/2000 | Cragg et al. | |
| 6,086,607 A | 7/2000 | Cragg et al. | |
| 6,090,130 A | 7/2000 | Nash et al. | |
| 6,126,675 A | 10/2000 | Shchervinsky et al. | |
| 6,143,006 A * | 11/2000 | Chan | 606/148 |
| 6,161,034 A | 12/2000 | Burbank et al. | |
| 6,162,192 A | 12/2000 | Cragg et al. | |
| 6,183,497 B1 | 2/2001 | Sing et al. | |
| 6,197,327 B1 | 3/2001 | Pruss et al. | |
| 6,200,328 B1 | 3/2001 | Cragg et al. | |
| 6,315,753 B1 | 11/2001 | Cragg | |
| 6,371,974 B1 | 4/2002 | Brenneman et al. | |
| 6,440,151 B1 | 8/2002 | Cragg et al. | |
| 6,440,153 B2 | 8/2002 | Cragg et al. | |
| 6,447,534 B2 | 9/2002 | Cragg et al. | |
| 6,503,222 B2 | 1/2003 | Lo | |
| 6,527,734 B2 | 3/2003 | Cragg et al. | |
| 6,533,802 B2 * | 3/2003 | Bojarski et al. | 606/232 |
| 6,540,735 B1 | 4/2003 | Ashby et al. | |
| 6,544,236 B1 | 4/2003 | Cragg et al. | |
| 6,547,806 B1 | 4/2003 | Ding | |
| 6,547,807 B2 * | 4/2003 | Chan et al. | 606/228 |
| 6,585,680 B2 | 7/2003 | Bugge | |
| 6,610,026 B2 | 8/2003 | Cragg et al. | |
| 2002/0002889 A1 | 1/2002 | Ashby et al. | |
| 2002/0016612 A1 | 2/2002 | Ashby et al. | |
| 2002/0038133 A1 | 3/2002 | Sing et al. | |
| 2002/0042378 A1 | 4/2002 | Reich et al. | |
| 2002/0049457 A1 * | 4/2002 | Kaplan et al. | 606/139 |
| 2002/0062104 A1 | 5/2002 | Ashby et al. | |
| 2002/0123750 A1 * | 9/2002 | Eisermann et al. | 606/69 |
| 2002/0156495 A1 | 10/2002 | Brenneman et al. | |
| 2003/0028140 A1 | 2/2003 | Greff et al. | |
| 2003/0088269 A1 | 5/2003 | Ashby | |
| 2003/0088271 A1 | 5/2003 | Cragg et al. | |
| 2003/0120258 A1 | 6/2003 | Ashby et al. | |
| 2003/0135237 A1 | 7/2003 | Cragg et al. | |
| 2003/0139773 A1 * | 7/2003 | Fisher et al. | 606/213 |
| 2004/0019328 A1 | 1/2004 | Sing et al. | |
| 2004/0019330 A1 | 1/2004 | Ashby | |
| 2004/0130155 A1 * | 7/2004 | Champion | 289/17 |
| 2004/0251688 A1 * | 12/2004 | Safwat et al. | 289/1.2 |

FOREIGN PATENT DOCUMENTS

| | | |
|---|---|---|
| EP | 0476178 | 3/1992 |
| EP | 0482350 | 4/1992 |
| EP | 0557963 | 2/1993 |
| EP | 0637432 B1 | 9/1994 |
| EP | 0637431 | 11/1994 |
| FR | 2641692 | 7/1990 |
| GB | 1509023 | 6/1980 |
| GB | 1569660 | 6/1980 |
| SU | 782814 | 11/1980 |
| SU | 1088709 A | 4/1984 |
| WO | WO 91/12847 | 9/1991 |
| WO | WO 94/02072 | 2/1994 |
| WO | WO 94/28800 | 12/1994 |
| WO | WO 95/28124 | 10/1995 |
| WO | WO 95/32669 | 12/1995 |
| WO | WO 95/32671 | 12/1995 |
| WO | WO 95/32679 | 12/1995 |
| WO | WO 96/08208 | 3/1996 |
| WO | WO 96/24290 | 8/1996 |
| WO | WO 97/07934 | 3/1997 |
| WO | WO 97/09934 | 3/1997 |
| WO | WO 98/06346 | 2/1998 |
| WO | WO 99/66834 | 12/1999 |
| WO | WO 2004/093649 | 11/2004 |

OTHER PUBLICATIONS

Allison; D., "Percutaneous Liver Biopsy and Track Embolization with Steel Coils," *Radiology*, vol. 169, 1998, p. 261.

Berman, Howard L., "Guided Direct Antegrade Puncture of the Superficial Femoral Artry," *American Ray Society Roentgen*, Sep. 1986, p. 632.

Berman, Howard L., "Modification of the Cope Drainage Catheter to Facilitate Placement," *American Ray Society Roentgen*, Jan. 1986, pp. 146, 169.

Bryne, J., "Endovascular Treatments for Intracranial Anuerysms," *The British Journal of Radiology*, 1996, pp. 98, 891.

Chuang, V., "Sheath Needle for Liver Biopsy in High-Risk Patience," *Radiology*, vol. 166, 1988, p. 261.

Correll, John T., "Certain Properties of a New Physiologically Absorbable Sponge," *Research Laboratories of the Upjohn Company*, 1944, p. 233.

Correll, John T., "Biologic Investigations of New Absorbable Sponge," *Research Laboratories of the Upjohn Company*, 1945, p. 585.

Di Seni, Ricardo, "Part 1, Embolotherapy: Agents, Equipment, and Techniques," *Vascular Embolotherapy*, vol. 4, p. 29.

Fandrich, C., "Small Guage Gelfoam Plug Liver Biopsy in High Risk Patients," *Australian Radiology*, vol. 40, 1996, p. 230. High Risk Patients, *Australian Radiology*, vol. 40, 1996, p. 230.

Foran, JPM, "Early Mobilization After Percutaneous Cardiac Catheterisation Using Collagen Plug (Vasoseal) Maemostatis," *BRHeart*, vol. 69, 1993, p. 424.

Gibbs, JSR, "Femoral Arterial Hemostasis Using a Collagen Plug After Coronary Artery Stent Implantation," *J. Interventional Card*, vol. 5, 1992, p. 85.

*Journal of Interventional Cardiology*, vol. 5, No. 2, June.

Kassell, "Size of Intracranial Aneurysm," vol. 12, No. 3, 1983.

Kiemeneiji, F., "Improved Anticoagulation Management after Palmaz Schatz Coronary Stent Implantation by Sealing the Arterial Puncture Site with Vascular Hemostasis Device," *Catheterization and Cardiovascular Diagnosis*, vol. 30, 1995, p. 1685.

Kussmaul, WG, "Rapid Arterial Hemostasis . . . Randomized Trial of a Novel Hemostatic Device," *J. Am. Coll. Card.*, vol. 25, 1995, p. 1685.

"Gelfoam Sterile Sponge, Sterile Powder and Sterile Film," *Pharmacia & Upjohn Manufacturer Brochure*, May 1997, p. 1.

"Gelfoam Sterile Powder," *Pharmacia & Upjohn Manufacturer Brochure*, Feb. 1996.

"Gelfoam Sterile Powder," *Pharmacia & Upjohn Manufacturer Brochure*, Mar. 1996.

"Gelfoam Sterile Sponge, Sterile Powder and Sterile Film," *Pharmacia & Upjohn Manufacturer Specification*, Nov. 1996, p. 1.

Riley, SA, "Percutaneous Liver Biopsy with Plugging of Needle Track: a Safe Method for Use in Patients with Impaired Coagulation," *The Lancet*, 1964, p. 436.

Saddekni, S., M.D., "Antegrade Catheterization of the Superficial Femoral Artery," *Radiology*, 1985, p. 531.

Sanborn, T., "Multicenter Randomized Trial Comparing Perutaneous Collagen Hemostasis Device with Conventional Manual Compression after Diagnostic Angiography and Angioplasty," *J. Am. Coll. Card.*, vol. 22, 1993, p. 1273.

Scharader, R., "Collagen Appl.," *Catheterization & Cardiovascular Diagnosis*, 1992, p. 298.

Schievink, "Intracranial Aneurysms," *The New England Journal of Medicine: Review Articles*, Jan. 2, 1997.

Silber, S., "Rapid Hemostasis of Arterial Puncture Sites with Collagen in Patients Undergoing Diagnostic Interventional Cardiac Catherterization," *Clinical Cardiology,* vol. 20, 1997, p. 981.

Smith, T., "Percutaneous Transhepatic Liver Biopsy with Tract Embolization," *Radiology,* vol. 198, 1996, p. 769.

Szikora, "Combined Use of Stents and Cells to Treat Experimental Wide-Necked Carotid Aneuryms: Preliminary Results," *AJNR AM Newradiol,* Jun. 1994, p. 1091.

Szikora, "Endovascular Treatment of Experimental Anuerysms with Liquid Polymers," vol. 38, No. 2, Feb. 1996.

Turjman, "Combined Stent Implantation & Endosacular Coil Placement for Treatment of Experimental Wide-Necked Aneurysms," *AJNRAM J. Neuroradio,* Jun. 1994, p. 1087.

Vogelzang, Robert L., "A Modified Cope Introducing Dilator to Allow Straight Guide Wire Introduction," *American Roantigen Ray Society,* Feb. 1986, p. 381.

Yoshimoto, "Cerebral Anuerysms Unrelated to Arterial Bifurcations," *Acta Neurochir (Wien),* 1996, pp. 138, 958.

Zins, M., "US-Guided Percutaneous Liver Biopsy with Plugging of the Needle Track," *Radiology,* vol. 187, 1992, p. 841.

(125) Ashby, Mark et al; U.S. Appl. No. 10/287,922, filed Nov. 4, 2002; entitled: Apparatus And Method For Inhibiting Blood Loss.

(130) Ashby, Mark et al; U.S. Appl. No. 10/069,107, filed Dec. 16, 2002; entitled: Device And Method For Determining A Depth Of An Incision.

(144) Ashby, Mark et al; U.S. Appl. No. 10/278,710, filed Oct. 22, 2002; entitled: "System and Method for Facilitating Hemostasis of Blood Vessel Punctures With Absorbable Sponge".

(152) Ashby, Mark et al; U.S. Appl. No. 10/334,770, filed Dec. 31, 2002; entitled: "Improved System and Method for Facilitating Hemostasis with Absorbable Sponge".

(159) Ashby, Mark et al; U.S. Appl. No. 10/462,065, filed Jun. 12, 2003; entitled: "Enhanced Bleed Back System".

(160) Ashby, Mark et al; U.S. Appl. No. 10/462,064, filed Jun. 12, 2003; entitled: "Release Mechanism".

(161) Ashby, Mark et al; U.S. Appl. No. 10/461,587, filed Jun. 12, 2003; entitled: "Dissolvable Closure Device".

(162) Ashby, Mark et al; U.S. Appl. No. 10/461,035, filed Jun. 13, 2003; entitled: "System And Method For Delivering Hemostasis Promoting Material To A Blood Vessel Puncture Site Using a Cannula".

(163) Ashby, Mark et al; U.S. Appl. No. 10/461,006, filed Jun. 13, 2003; entitled: "System and Method for Delivering Hemostasis Promoting Material to a Blood Vessel Puncture with a Staging Tube".

(164) Ashby, Mark et al; U.S. Appl. No. 10/460,859, filed Jun. 12, 2003; entitled: "Hemostatic Device Including a Capsule".

(187) Ashby, Mark et al; U.S. Appl. No. 10/732,441, filed Dec. 9, 2003; entitled: "Pledget-Handling System and Method for Delivering Hemostasis Promoting Material to a Blood Vessel Puncture Site By Fluid Pressure".

(190) Ashby, Mark et al; U.S. Appl. No. 10/754,824, filed Jan. 9, 2004; entitled: "Sheath-Mounted Arterial Plug Delivery Device".

* cited by examiner

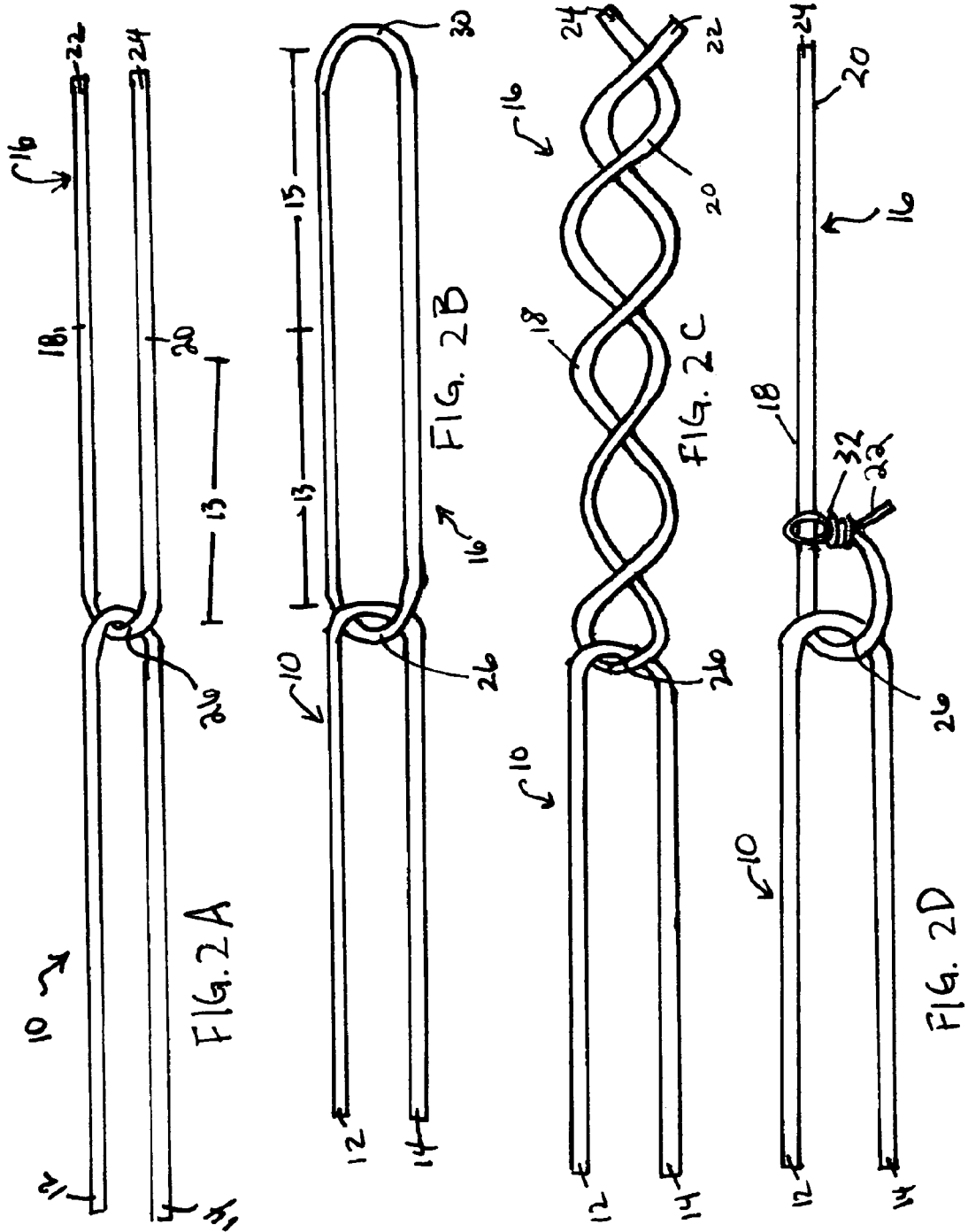

CINCHING LOOP

CROSS REFERENCE TO RELATED APPLICATIONS

This application claims priority on Provisional Application Ser. No. 60/528,383, entitled, "Cinching Loop", by inventors Mark Ashby, Roy D. Bertolet, Tin T. Tran and Andrew H. Cragg, filed on Dec. 9, 2003.

FIELD OF THE INVENTION

The present invention relates to cinching loops for use in interventional and surgical procedures. More particularly, the present invention relates to cinching loops for use in interventional and surgical procedures which may be used with pressure plugs, hemostatic pledgets, hemostatic knot pushers, and the like.

BACKGROUND OF THE INVENTION

Suturing tissue or organs is a tedious and delicate procedure. This is due principally to the use of one single strand of suture thread, the thinness of the suturing thread, as well as its tendency to twist about its length. In one type of suturing procedure, the thread is directed through a tissue and the free ends thereof are wrapped to define a half-hitch knot that froths a closed loop, the diameter of which can be reduced ultimately to the point that the thread is cinched at the tissue. As twisting of the thread occurs, restriction of the loop is inhibited, possibly to the point that it is impossible to cinch the knot at the body tissue, as required. Even after one half-hitch knot is formed and properly cinched, the twisting problem persists and may interfere with, or prevent, the subsequent formation of additional half-hitch knots as would "lock" the suture. When this occurs, the surgeon may be required to cut the suture and re-start the process. This process is time consuming. These problems increase the overall time of the operation and contribute undesirably to hand, and overall, surgeon fatigue.

Most suture knots are tied completely by hand or, in instances where the fingers cannot reach, using surgical instruments. Certain apparatuses have been proposed which assist in forming suture knots. However, the prior apparatuses and associated methods of use provide assistance only in tying relatively simple knots or only small portions of more complicated knots.

Other common knots used for sutures are the square and the surgeon's knots. The square knot is a simple knot, but difficult to fashion solely with surgical instruments such as are necessary in endoscopic surgical procedures. However, once formed, the square knot may easily become untied.

Impetus for developing improved knots along with practical methods and apparatuses for their formation arises from the advancements and greater utilization of endoscopic procedures. Endoscopic and interventional procedures are currently hampered by the inability to easily tie knots within the body and other relatively inaccessible involved spaces. FIG. 1 illustrates a single strand of suture used to seal a blood vessel puncture site. As described above, suture knots are formed utilizing one single strand of suture thread 102. One method to tie a knot is by inserting a needle into a hollow body cavity, passing the needle through the tissue or blood vessel wall 104, bringing the needle out to the exterior, creating a tissue cinching loop 106 by manually developing a knot 108 and then locking the tissue cinching loop 106 into position by pulling on the end of the suture 101.

Currently, to release the tissue cinching loop 106 within the patient, the skin of the patient is depressed and the thread 102 is cut at some level below the skin. The acts of depressing and cutting are extra steps that a surgeon must perform. Furthermore, having the thread near the skin may increase the chance of infection to the patient. Additionally, the tissue cinching loop 106 may not adequately close the puncture site 110 causing blood to flow out of the blood vessel. Moreover, the entire suture thread 102 directly contacts the tissue or blood vessel wall 104 which may cause lacerations and tearing of the tissue 104 resulting in additional injury and requiring additional repair to the blood vessel puncture site 110.

Another method to perform the suturing in the interior of the body, is with the use of a curved needle with a fine suturing thread. It is held with a gun-shaped needle holder or grasper. The needle holder includes a clamp to securely hold the needle. The clamp can be rotated through 360° for maneuvering the needle to perform the desired stitching. The drawbacks of endoscopic and similar surgery are both the distance the suturing site is located inside the body as well as the limited space available within the body since manipulation of the surgical instruments themselves are used for the suturing process. With respect to the latter, a problem arises in manipulating the curved needle to easily tie a knot to close the surgical incision in situ. Many manipulations of the needle, needle holder, and suture thread are required for each suturing knot that is placed at the incision site.

Suture knots may also be used with other apparatuses such as an anchor and pulley system, suture pusher, and the like. However, significant limitations relating to current apparatuses and methods for the formation of suture knots include: (1) being limited to the formation of simple knots such as the square knot; (2) involving knots which require the manipulation of both ends of a length of suture filament which, accordingly, cannot be substantially tied prior to surgery or merely slipped into place; (3) requiring multiple manipulations outside of the surgical incision with loops thereby formed being afterwards coaxed toward the suture site; and (4) requiring the depression of the skin surface and cutting of excess suture from the body.

Extra-corporeal suturing, knots being tied outside the body to thereafter be slipped into position, has also been used in the past. It requires directing a suture carrying needle through a cannula, through internal body tissue, and out the proximal end of the cannula so that the free ends of the suturing thread are accessible from externally of the cavity. The surgeon then manipulates the free ends of the suturing thread by wrapping the threads in such a manner as to define a cinching loop in the form of a half-hitch knot. An elongate "pusher" rod, with a bifurcated free end, is engaged with one of the free ends of the thread in the vicinity of where they are wrapped and pressed through the cannula, while at the same time holding both free thread ends projecting away from the loop. As this takes place, the cinching loop diameter restricts to the point that it is ultimately cinched at the tissue.

This procedure is convenient from the standpoint that the half-hitch knots can be formed from externally of the body cavity. However, this introduces other complications. The problem of thread tangling persists. Further, the procedure is inherently awkward by requiring that the free ends of the suture projecting away from the loop be held taut as a pusher is pressed through the cannula to reduce the loop diameter. Thus, there are three manipulation points—the two free ends of the thread projecting away from the loop must be held and one of the threads at the wrapped portion of the loop must be pressed through the cannula. The result is that the procedure may require two sets of hands.

Further, the thread is prone to escaping from the open free end of the pusher. When this occurs, the surgeon is required to attempt to reposition the thread in the pusher end. This is a difficult and time consuming procedure that may be made impossible by twisting of the thread that occurs within the cavity. The end result of this may be that the surgeon may be required to remove the partially locked suture and re-start the procedure.

Additionally, since the thread is prone to twisting, the thread may bind as the loop diameter is restricted. Excessive pressure exerted by the pusher on the thread with this condition may result in thread breakage and/or damage to the tissue.

Sutures may be used for many reasons, including the formation of cinching loops. One reason for the use of a cinching loop is to limit blood flow, in tourniquet-fashion, from blood vessels termed "bleeders" or to close arterial punctures. Another may be to join two organs or the like together. Another may be to secure an object at a certain position. Whatever the reason for the use of a cinching loop, there exists a need for an more efficient, less complicated, safer, and simple way to form and release the cinching loop within the body.

BRIEF DESCRIPTION OF THE INVENTION

A solution is provided to release a cinching loop within a body having a first thread having a first end and a second end, and a second thread having a first half having a first tip, a second half having a second tip, a bottom half having a link, and a top half, wherein the first end is inserted through the link. A first knot is formed around the first thread with the top half thereby forming a loop where the diameter of the loop decreases as the knot is pushed into the body and the first thread is pulled out of the body and where the loop is released within the body when the first end is pulled out of the body.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

Link

In the drawings:

FIG. 1 illustrates a suture used to seal a blood vessel puncture site.

FIGS. 2A, 2B, 2C, and 2D illustrate embodiments of the present invention.

FIGS. 3A, 3B, 3C, and 3D illustrate an embodiment of the present invention at a blood vessel puncture site.

Figure 4A:
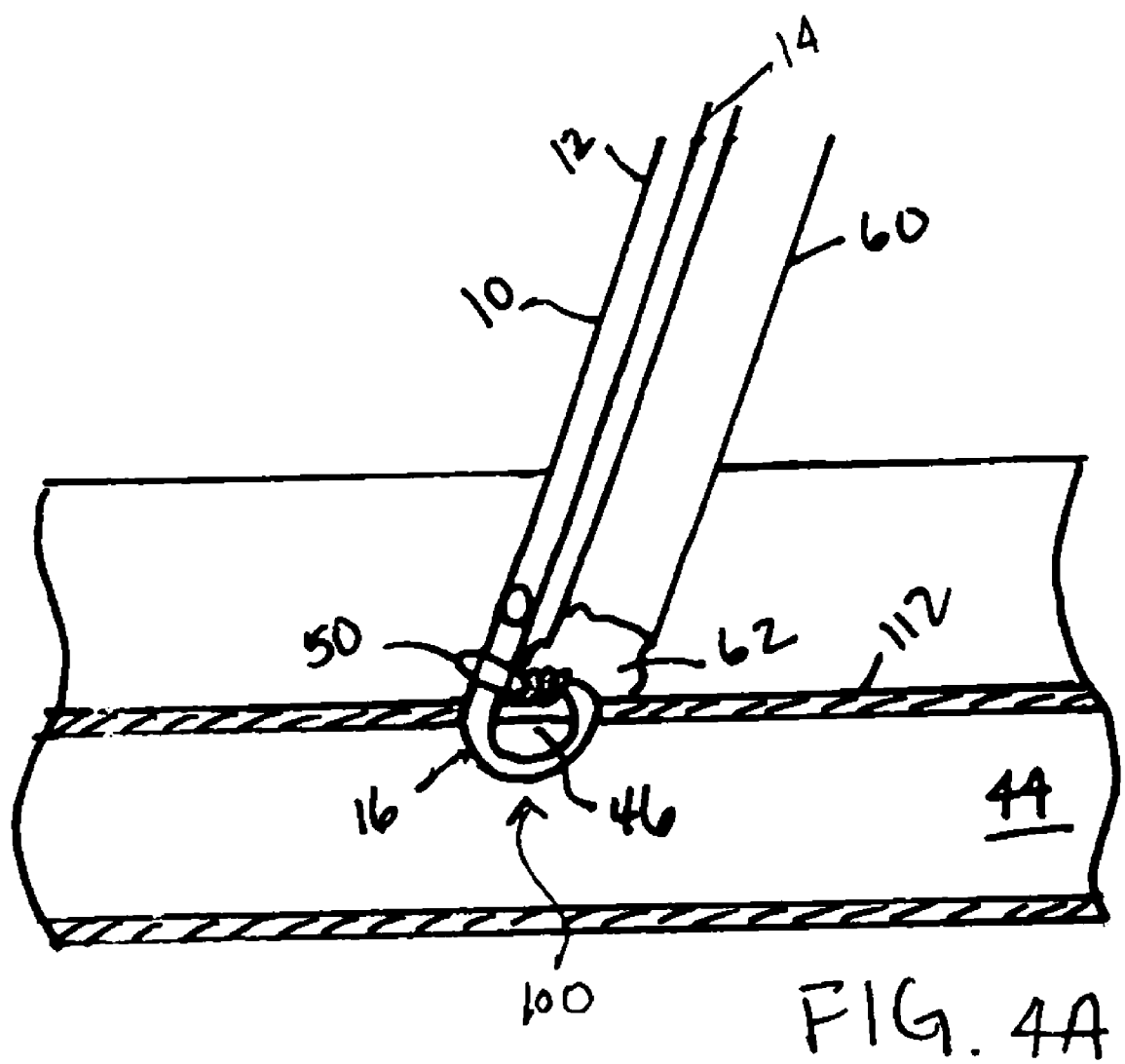
Figure 4B:
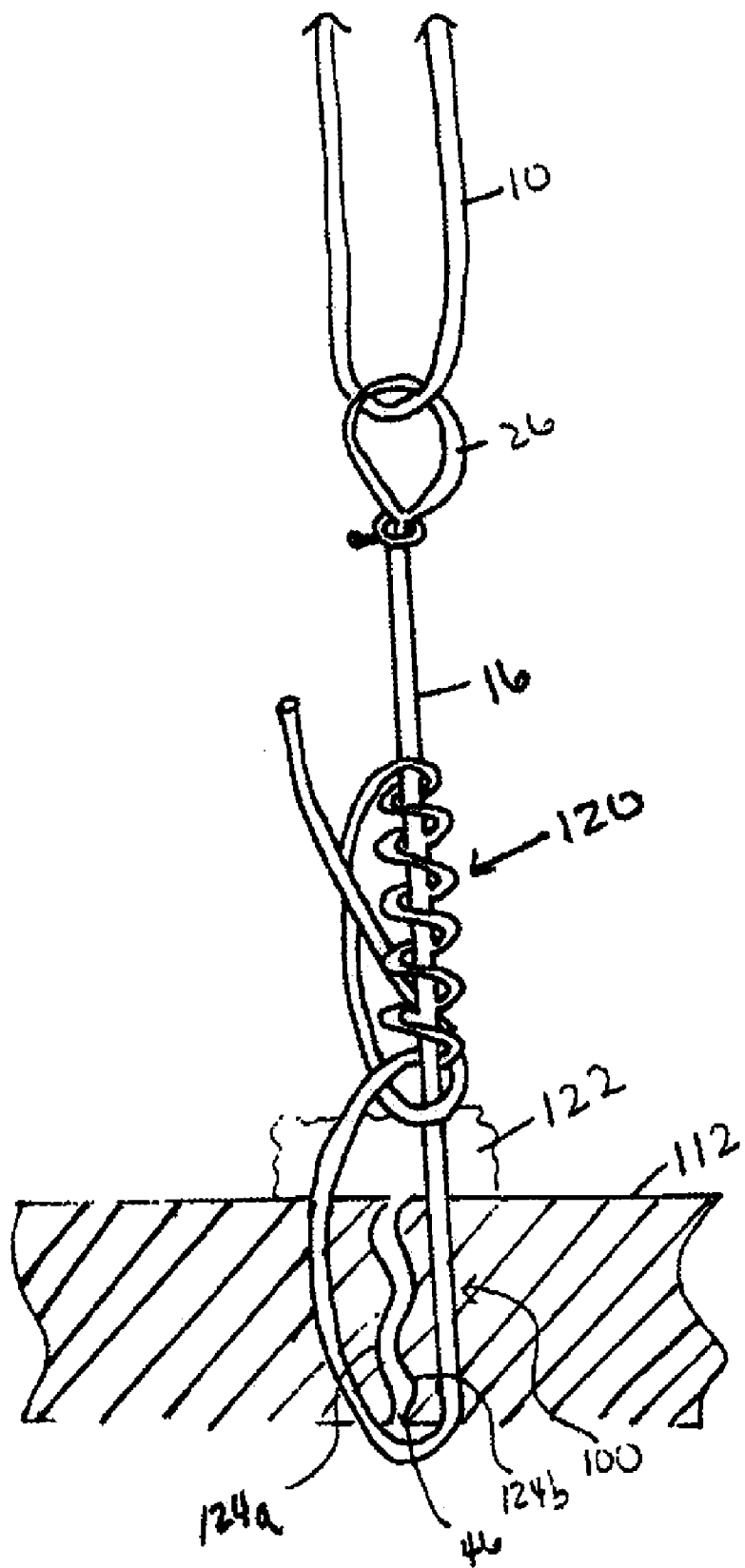

FIGS. 4A and 4B illustrate the cinching loop used in combination with a sheath and hemostatic promoting material in accordance with an alternative embodiment of the present invention.

Figure 5A:
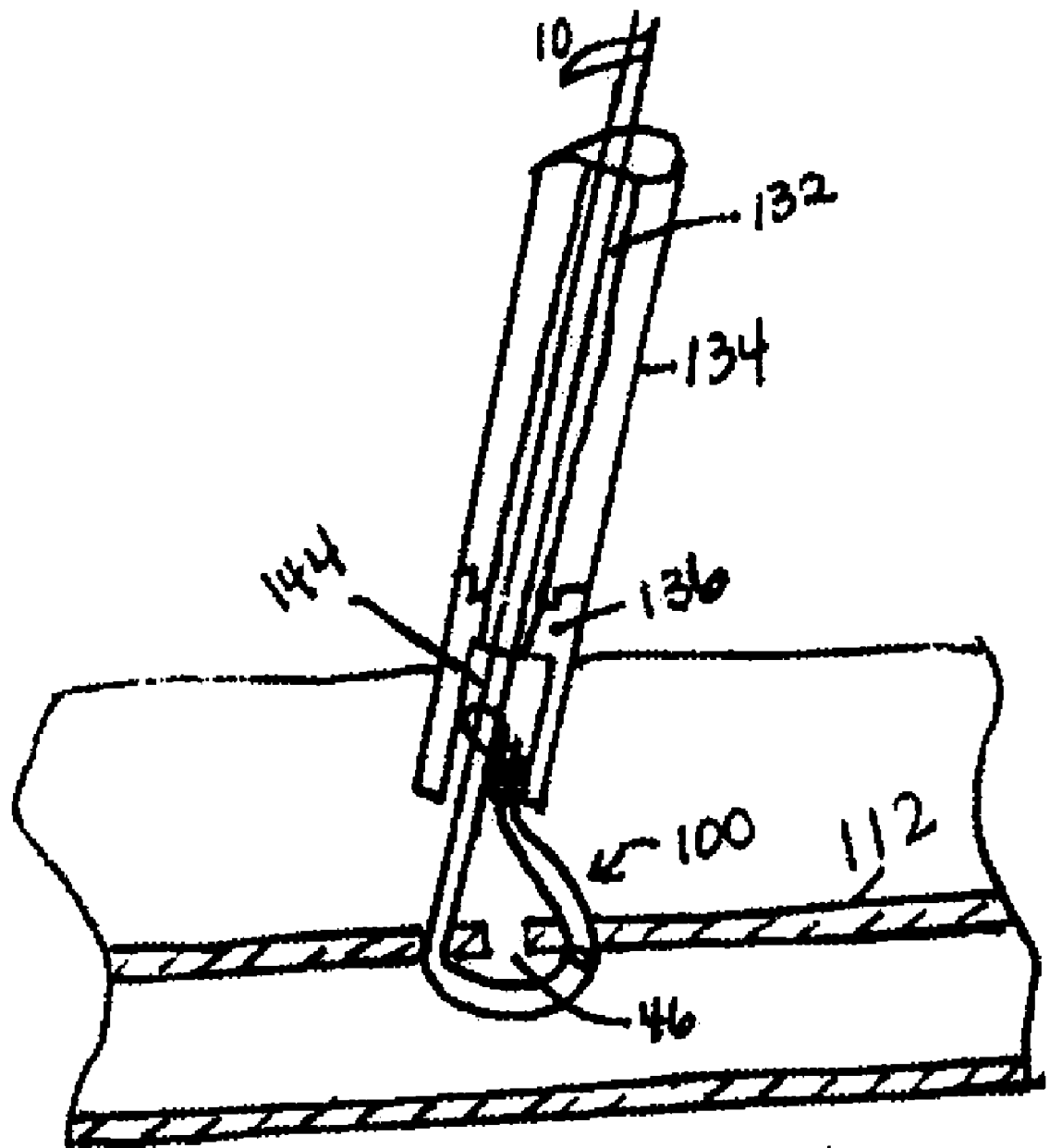
Figure 5B:
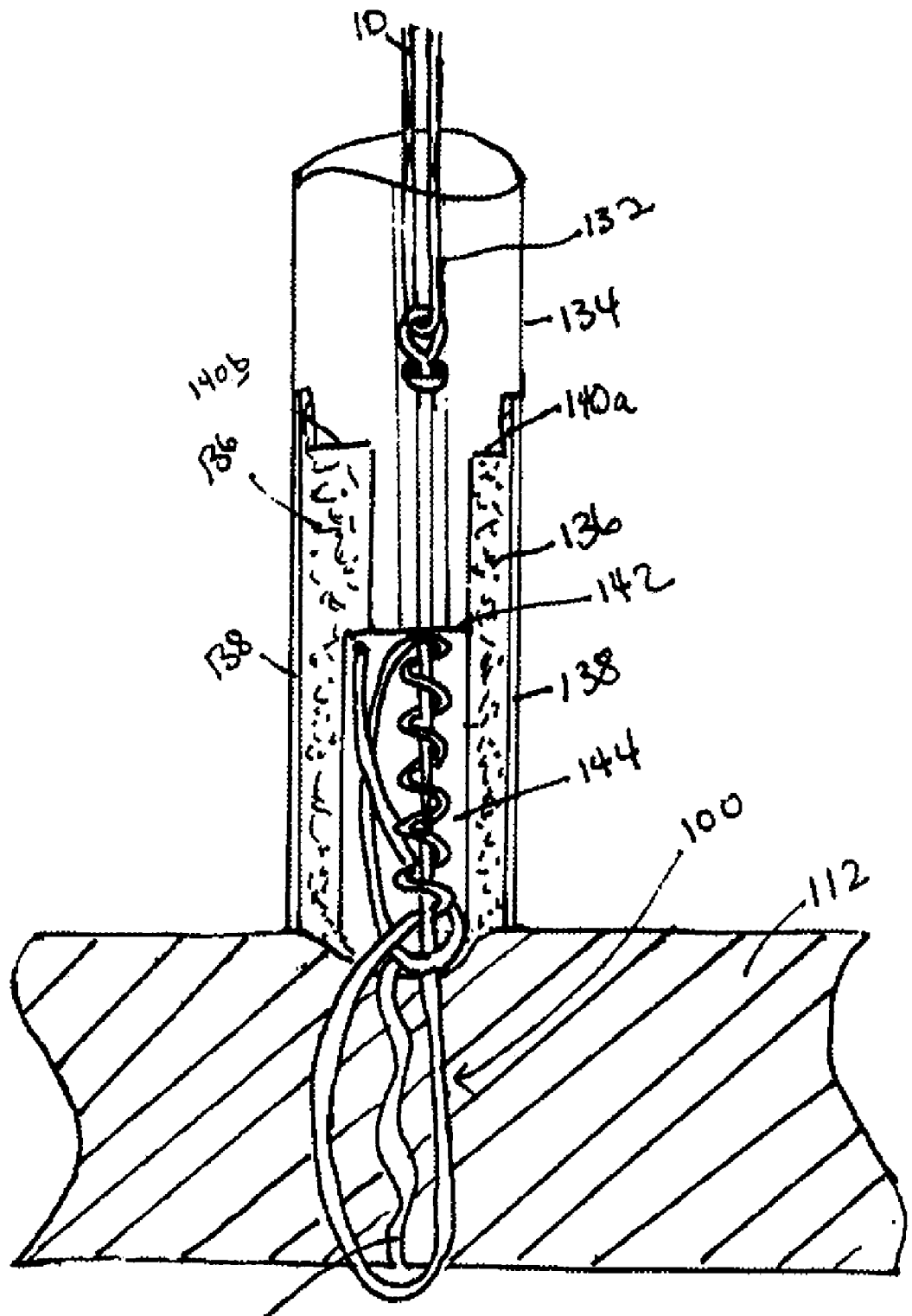

FIGS. 5A and 5B illustrate the cinching loop used in combination with a pusher and hemostatic promoting material in accordance with an embodiment of the present invention.

FIGS. 6A, 6B, 6C, 6D, and 6E illustrate the cinching loop used in combination with a pressure plug in accordance with an embodiment of the present invention.

Figure 7:
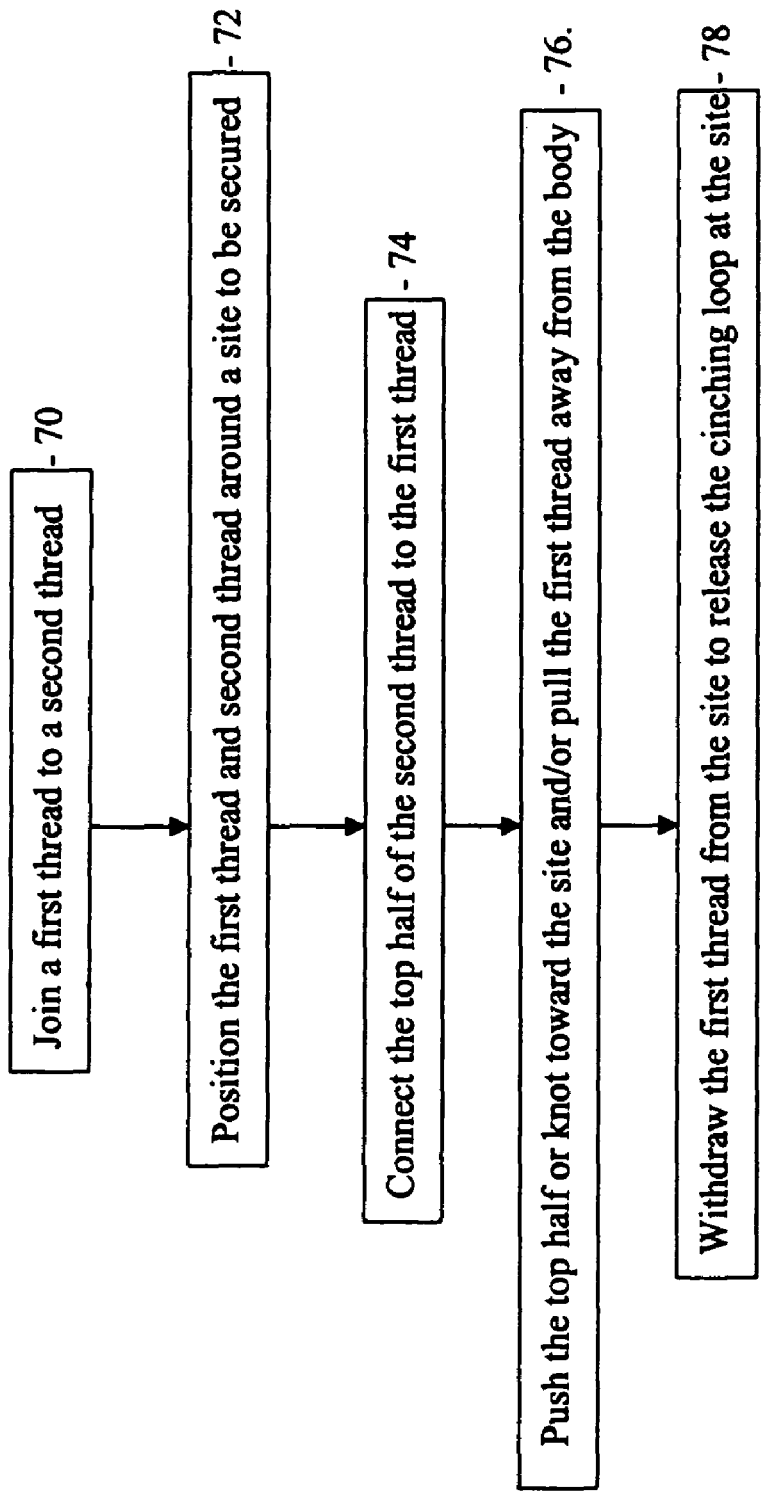

FIG. 7 is a block diagram illustrating a method for releasing a cinching loop within a body.

DETAILED DESCRIPTION

Embodiments of the present invention are described herein in the context of a cinching loop. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

A solution is provided for a self-forming and self-releasing cinching loop. The cinching loop may be used to seal a blood vessel puncture site, to hold two or more organs or the like together, or secure an object or organ at a certain position or location. The self-forming and self-releasing cinching loop is a more efficient, less complicated, safer and simple way to form and release a cinching loop within a body with the use of two strands of suture thread.

FIGS. 2A-2D illustrate embodiments of the present invention. Referring to FIG. 2A, a first thread, generally numbered 10, has a first end 12 and a second end 14. A second thread, generally numbered 16, has a first half 18 and a second half 20. The first half 18 having a first tip 22 and the second half 20 having a second tip 24. As illustrated in FIG. 2A, first thread 10 may be linked with second thread 16 through link 26, which may be achieved by inserting the first end 12 through the link 26 and then matching the first end 12 with the second end 14. The link 26 may be positioned at a bottom half 13 of the second thread 16, wherein the bottom half 13 may be the same length as top half 15. The length of first thread 10 and second thread 16 may vary according to use of the cinching loop. However, it is preferable that first thread 10 be longer in length than second thread 16.

The link 26 may be formed by folding the second thread 16 in half to from the first half 18 and the second half 20 as illustrated in FIG. 2A. However, the link 26 may be formed by any other means. By way of example only, and not meant to be limiting, the link 26 may be formed by connecting the first tip 22 to the second tip 24 which will also form a link 30 at the top half 15 of the second thread 16 as illustrated in FIG. 2B. The first tip 22 and second tip 24 may be connected with any bioabsorbable sealing material. Types of sealing material may be any biocompatible polymers such as PGA, gelatin, mannitol and the like. First tip 22 and second tip 24 may also be tied together with a knot (not shown), or any other like manner. In another example, as illustrated in FIG. 2C, the first half 18 may be twisted around the second half 20 thereby forming a braid-like shape to form link 26. In yet another example, shown in FIG. 2D, first tip 22 may be tied to first half 18 with a knot 32, or any other means, to form link 26.

Figure 1:
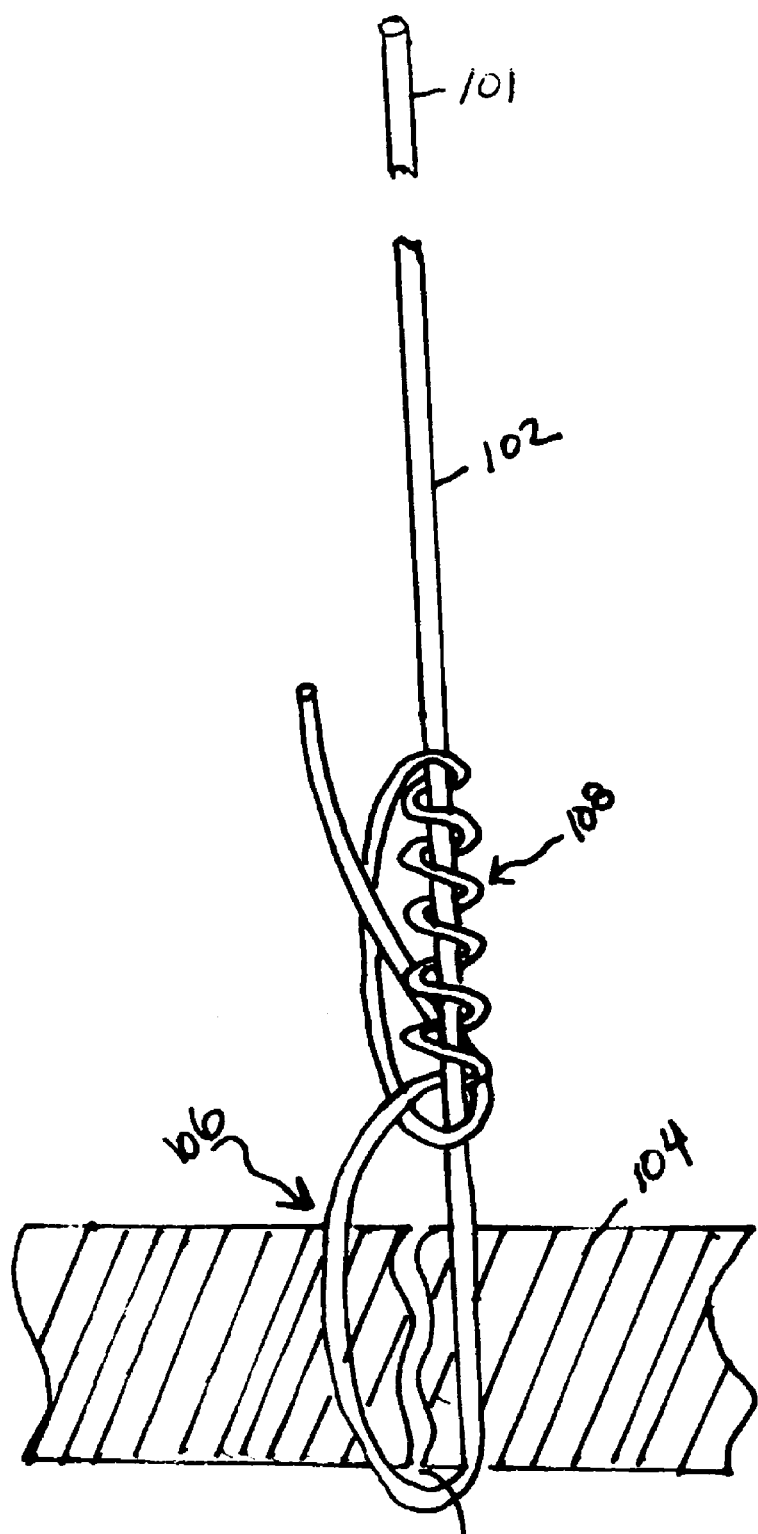
Figure 3A:
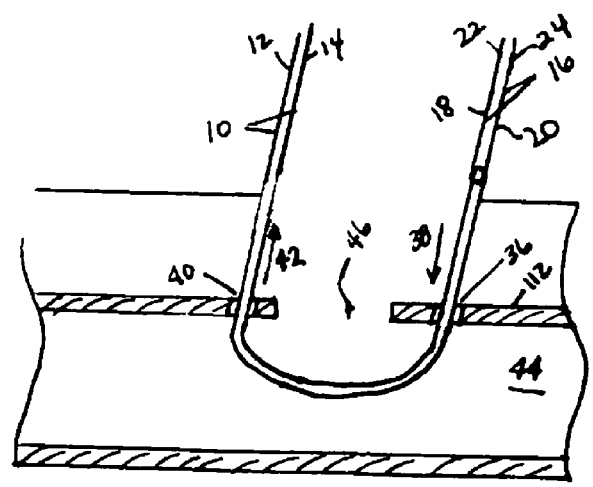

FIGS. 3A-3D illustrate an embodiment of the present invention at a blood vessel puncture site. FIG. 3A illustrates the first thread 10 linked with the second thread 16. The first thread 10 may be inserted into a first opening 36 in the direction of arrow 38 into a blood vessel lumen 44 and out a second opening 40 in the direction of arrow 42 Alternatively, first thread 10 may then be pushed into the blood vessel lumen 44, first thread 10 may be pulled out of first opening 36 in the direction opposite of arrow 38. First opening 36 and second opening 40 are illustrated at each end of the blood vessel puncture site 46 It will be appreciated that first opening 36 and second opening 40 are illustrated as large holes for illustration purpose only Rather, the first and second openings are actually small slits where the thread would pierce through the blood vessel wall and not allow blood to flow out of. There are many well known methods that may be used to insert the suture thread through the blood vessel wall 112, such as with the use of a curved needle as described above and will not be described herein so as not to overcomplicate the present disclosure.

Figure 3B:
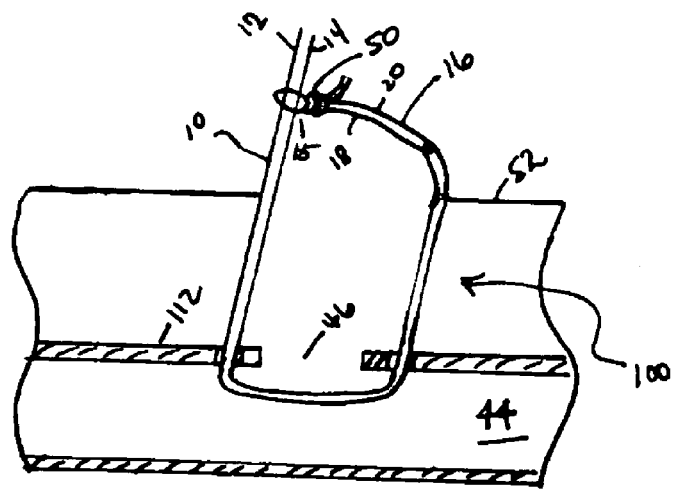

Referring now to FIG. 3B, illustrating the second thread joined to the first thread to form the cinching loop. The second half 15 of the second thread 16 may be joined to the first thread 10 with a knot 50 thereby forming the cinching loop, generally numbered 100. The knot may be a self-securing knot such that it may move along first thread 10 toward the blood vessel puncture site 46, but will resist moving away from the blood vessel puncture site 46. Various knots are well known and used by those of ordinary skill in the art. Any knot, such as a square knot or any other type of surgical knot, may be used in the present invention. The various types if knots that may be used will not be described herein so as not to overcomplicate the present disclosure. If the embodiment of FIG. 2D is used, only the second tip 24 would be joined to the first thread 10.

Figure 3C:
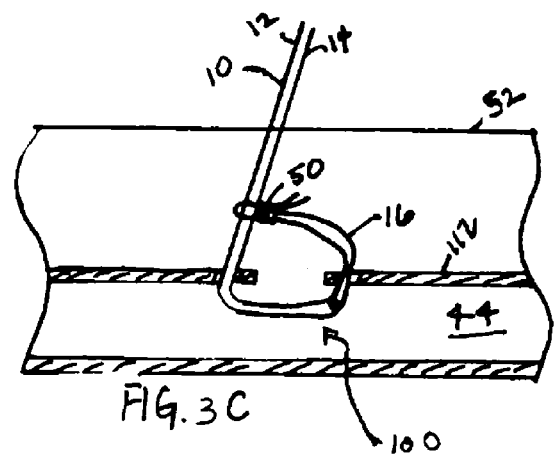

FIG. 3C illustrates the first the embodiment of FIG. 3B at a later time. The first thread 10 may be kept taught and used as a rail to push the knot 50 down toward the blood vessel puncture site 46 by pulling the first thread 10 away from the skin surface 52. The knot 50 may also be pushed down with any instrument, such as with the use of a sheath 60, as illustrated in FIG. 4A. This may cause the cinching loop 100 to decrease in diameter and size.

Figure 3D:
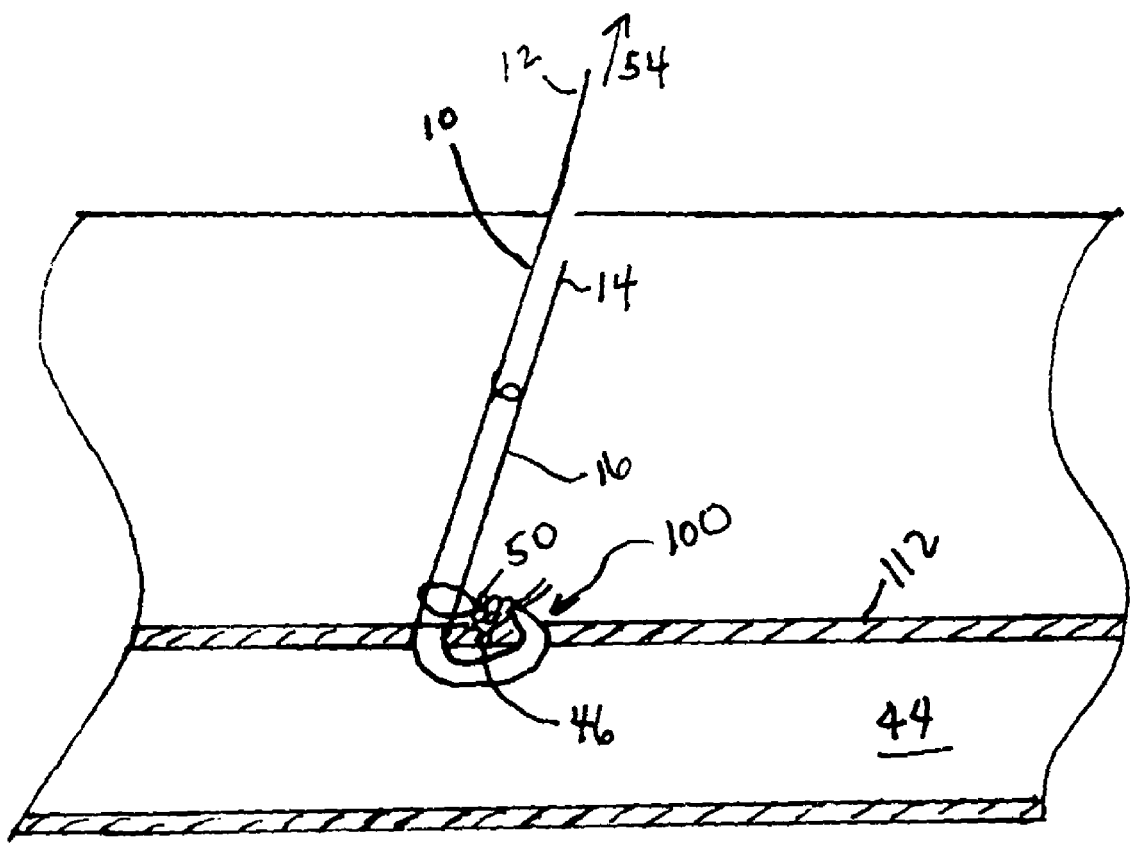

FIG. 3D illustrates the cinching loop formed around the blood vessel puncture site to promote hemostasis. As the knot 50 is pushed toward the blood vessel puncture site 46, either from above the puncture site with an apparatus and/or pulled by tension on first thread 10, the cinching loop 100 decreases in size or diameter until it is cinched at the blood vessel puncture site 46. The cinching loop 100 holds the adjacent blood vessel puncture surfaces together to seal the blood vessel puncture site 46. At this point, the knot 50 is positioned around the second thread 16. Once the cinching loop 100 is tight around the blood vessel puncture site 46, the first thread 10 is withdrawn from the body by releasing the second end 14 and pulling the first end 12 out of the body in the direction of arrow 54. A secure cinching loop 100 is formed at the blood vessel puncture site 46 and is easily released at the site by simply withdrawing the first thread 10.

The cinching loop of the present disclosure may be used with any other current devices and apparatuses such an anchor and pulley system. The examples described in Examples 1, 2, and 3 with reference to FIGS. 4A, 4B, 5A, 5B, 6A-6E are for exemplary purposes to illustrate various uses of the present disclosure and not intended to be limiting.

Example 1

FIGS. 4A-4B illustrate the cinching loop used in combination with a sheath and hemostatic promoting material in accordance with an alternative embodiment of the present invention. A sheath 60, or any other device such as a pusher, may be used to push the knot 50 toward the blood vessel puncture site 46. The sheath 60 may also deliver a hemostasis promoting material 62 to the puncture site 46 to ensure that hemostasis occurs at the puncture site 46 and within the adjacent tissue tract. Thus, the sheath 60 may act both as a pusher and a hemostatic promoting material delivery device.

Alternatively, the cinching loop may be used to position the hemostatic promoting material at the blood vessel puncture site as illustrated in FIG. 4B. With the hemostatic promoting material 122 in position at the blood vessel puncture site 46, the tissue cinching loop 100 initially formed by joining thread 16 to thread 10 such that the first and second segments of the first thread pass through a second link or loop 120 in thread 16 may be used to secure the hemostatic promoting material 122 in position at the puncture site 46 while drawing tissue 124a and 124b together to close the puncture site. The hemostatic promoting material 122 may be positioned at the puncture site 46 before being cinched in position or the hemostatic promoting material 122 may be inserted down the suture thread, using the first thread 10 as a positioning means, and then cinched in position with the cinching loop 100 in second thread 16. This prevents and stems bleeding in case the puncture was poorly closed and helps to reduce tract oozing or blood flow out of the tissue tract.

Example 2

FIGS. 5A and 5B illustrate the cinching loop used in combination with a pusher and hemostatic promoting material in accordance with an embodiment of the present invention. Referring to FIG. 5A, when the cinching loop 100 is positioned around the blood vessel puncture site 46, the first thread 10 may be received by a lumen 132 of a pusher 134. This allows the user to keep first thread 10 taught or tensioned around the blood vessel puncture site 46. FIG. 5B illustrates the cinching loop and pusher at the blood vessel puncture site. The pusher 134 may have a hemostatic promoting material 136 positioned around a portion of the lumen 132 at the distal end 142 of the pusher 134. The hemostatic promoting material 136 may be surrounded by a dissolvable capsule 138, such as a gelatin capsule. When the capsule 138 is exposed to blood or other fluids, the capsule will dissolve thereby releasing the hemostatic material 136. The hemostatic material may then absorb the fluids and expand to provide hemostasis at the puncture site 46 in situations where the puncture 46 is not sealed properly and/or to reduce blood flow out of the tissue tract.

The capsule 138 may be made from gelatin and formulated to have flexibility (like a gel-cap vitamin E) or be stiff like a typical 2-piece oral capsule. Capsules are made to dissolve within a predetermined time, with a dissolution time between 10 seconds and 10 days, and normally between one minute and 10 minutes. Also, the capsule 138 can be formulated to be inert (e.g. non thrombogenic, non-bacteriostatic) or to provide/deliver therapeutic benefit (e.g. bacteriostatic, clot acceleration which may include clot accelerators such as thrombin, calcium based compounds, chitosan, and may also include antibiotics or radiopaque substances). The capsule 138 can vary in characteristics along its length. For example, the distal region can be inert while the proximal region comprises therapeutic material.

The pusher may have shoulders 140a, 140b to push the hemostatic capsule into the tissue tract. The capsule 138 may contain an opening 144 to receive a portion of the cinching loop 100. As the pusher 134 is pushed toward the blood vessel puncture site 46, the cinching loop 100 is received by the opening 144 and the distal end 142 of the pusher 134 pushes the cinching loop 144 toward the puncture site 46. As the cinching loop 100 is pushed toward the puncture site 46, the first thread 10 is withdrawn from the pusher 134. This causes the tissue cinching loop 144 to decrease in size and diameter. Once the cinching loop 100 is positioned at the puncture site 46, the pusher 134 may be withdrawn thereby releasing the capsule 138 and hemostatic promoting material 136 at the blood vessel puncture site 46. The cinching loop 100 may then be released in the patient by withdrawing first thread 10 as described above.

Various hemostasis promoting materials may be used such as fibrillar collagen, collagen sponge, regenerated oxidized cellulose, gelatin powder, hydrogel particles, or gelatin sponge. The first thread and second thread may be made of any semi-rigid, absorbable or non-absorbable, biocompatible suture material known to those of ordinary skill in the art.

Example 3

Figure 6A:
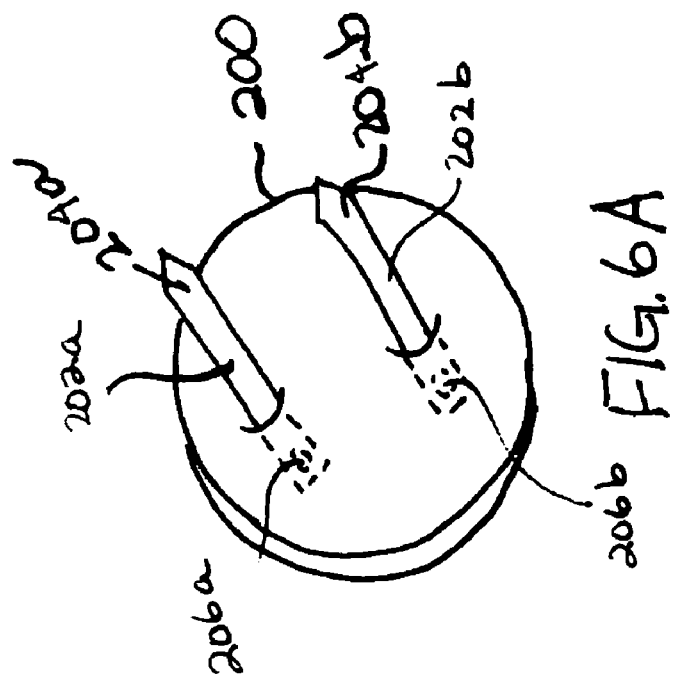
Figure 6B:
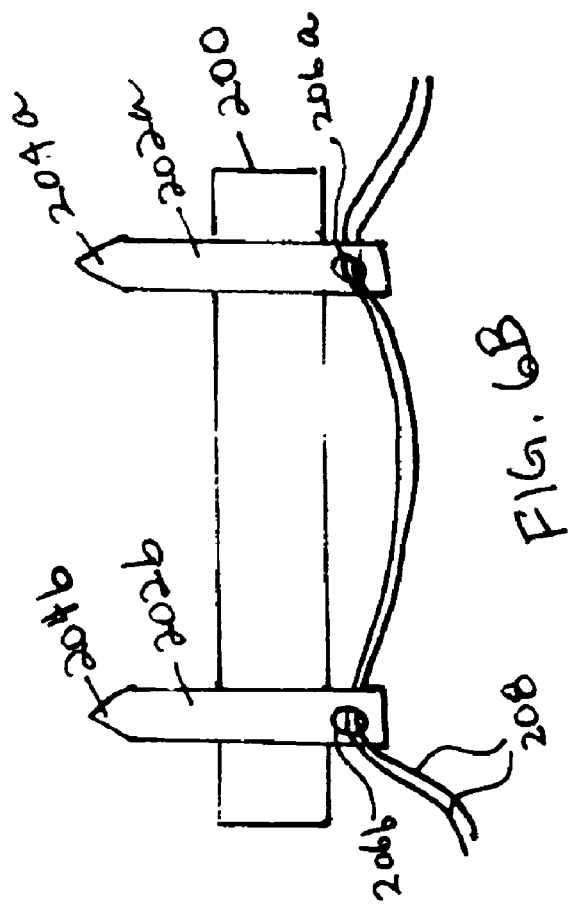

FIGS. 6A-6E illustrate the cinching loop used in combination with a pressure plug in accordance with an embodiment of the present invention. The pressure plug is described in detail in United States published patent application no. 2007/0282373 filed Nov. 24 2004, entitled "Hemostatic Pressure Plug" by inventors Mark Ashby, Roy D. Bertolet, Andrew Cragg, and Tin Tran, which is incorporated by reference herein in its entirety. FIGS. 6A and 6B illustrate the pressure plug 200 having suture retrieval needles 202a and 202b. The suture retrieval needles 202a, 202b may be secured on the pressure plug 200 with any absorbable and/or sealing material as described above. The suture retrieval needles 202a, 202b may be made of any biocompatible, flexible, durable material that will allow the needles 202a, 202b to be in a collapsed position for delivery within a patient, retract and retain its shape when exposed within the blood vessel lumen, and be able to pierce the blood vessel wall. The suture retrieval needle may be of any length necessary to allow the needle to be retrieved and therefore may need to be folded within the sheath for delivery to the blood vessel puncture site. Examples of semi-rigid, absorbable, biocompatible materials are Collagen, Oxidized Cellulose, PGA, methyl cellulose, carboxymethyl cellulose, carbowaxes, gelatin (particularly pigskin gelatin), urethane foam, and sugar based compounds. Among other suitable polymers are polylactic glycolic acids, polyvinyl pyrrolidone, polyvinyl alcohol, polyproline, and polyethylene oxide.

Figure 6C:
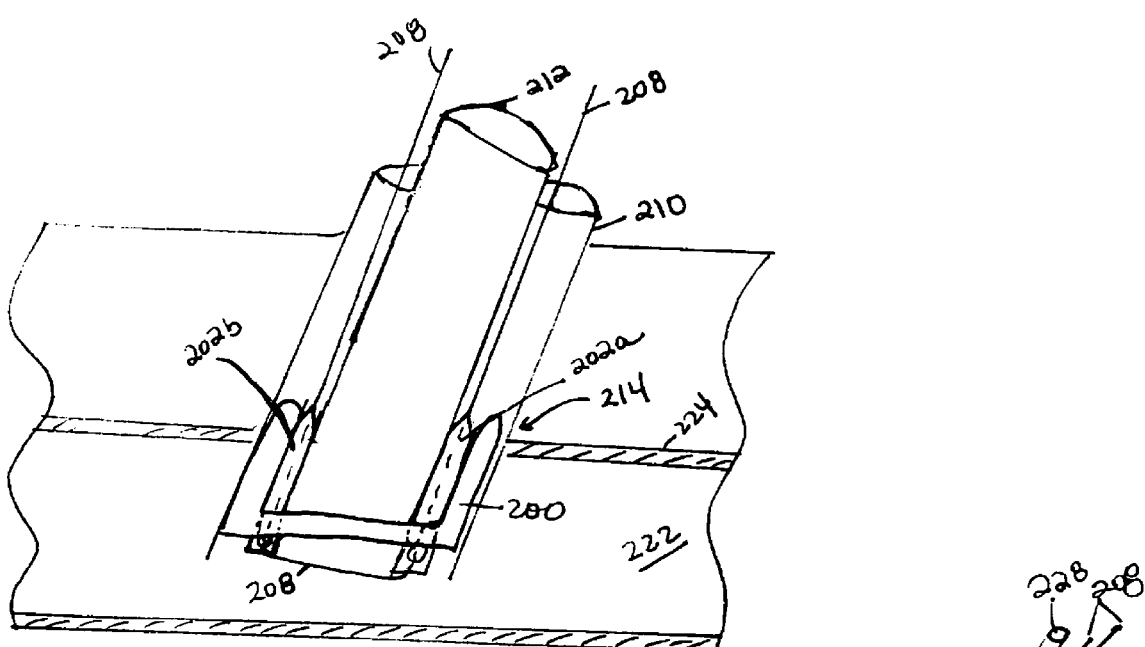
Figure 6D:
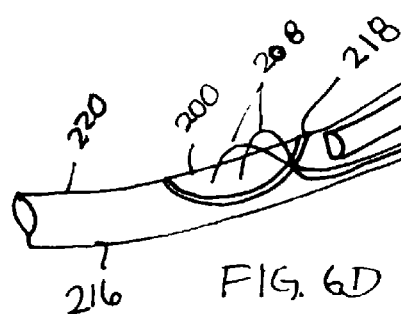
Figure 6E:
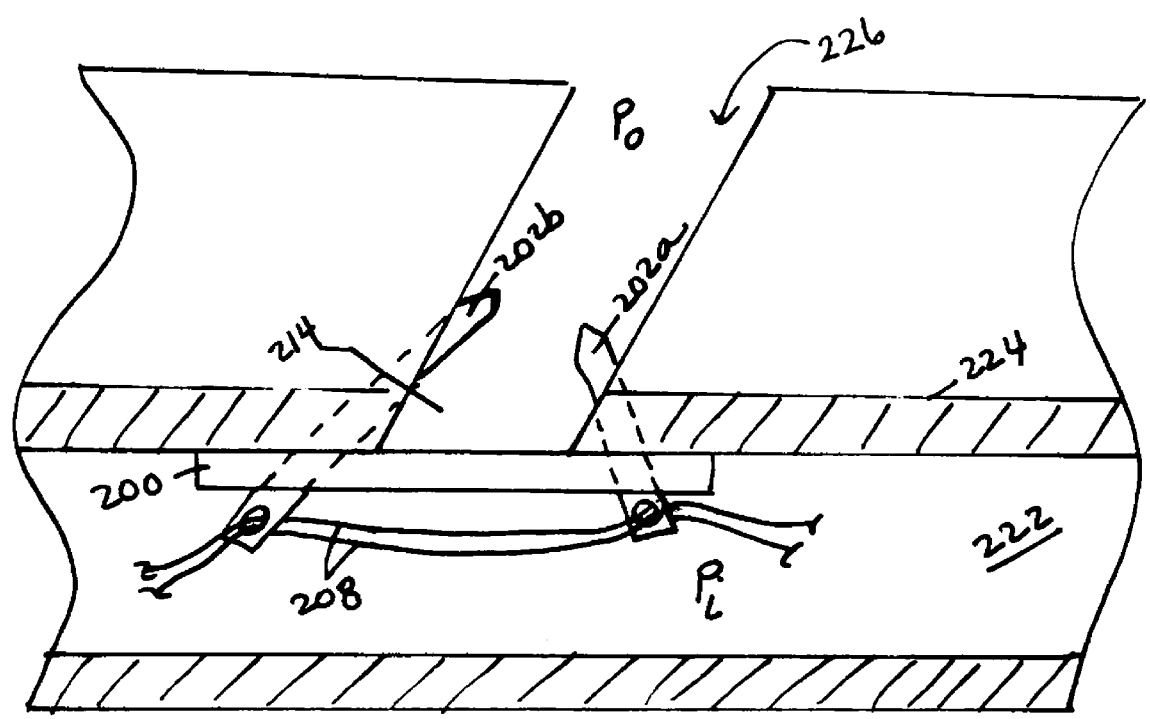

The suture retrieval needles 202a, 202b may be positioned anywhere on the pressure plug 200, but should be positioned in a location that will allow the suture retrieval needles 202a, 202b to pierce the blood vessel wall 224 as illustrated in FIG. 6E. The suture retrieval needles 202a, 202b may have blunt tip 204a, 204b, but should be sharp enough to pierce the blood vessel wall 224. The suture retrieval needles 202a, 202b may have an opening 206a, 206b to insert the suture thread 208. However, the suture thread 208 need not be attached to the needles 202a, 202b through the openings 206a, 206b. Rather, the suture thread 208 may be attached to the suture retrieval needles through other means such as with any of the sealing materials described above.

Referring to FIG. 6C, the plug 200 may be pushed through a sheath 210 with a pusher 212 to the blood vessel puncture site 214. The suture thread 208, pressure plug 200, and suture retrieval needles 202a, 202b are in a collapsed position when inserted in the sheath 210 for delivery to the blood vessel puncture site 214. There are other ways to deliver the pressure plug 200 to the blood vessel puncture site, such as with a cannula 216 having an opening 218 at a bottom end 220 of the wall of the cannula 216 as illustrated in FIG. 6D. The plug may be delivered with a foot plate 228 or pusher. However, not all methods of delivery will be discussed herein to prevent obfuscation of the present disclosure.

Once the pressure plug is delivered within the blood vessel lumen 222, the pressure plug 200 and suture retrieval needles 202a, 202b expand to its original shape. The pressure difference between the inside of the blood vessel lumen 222 and outside the blood vessel lumen (i.e. such as the tissue tract 226) causes the pressure plug 200 to be suctioned against the blood vessel puncture site 214 as illustrated in FIG. 6E. In essence, the pressure inside $P_i$ the blood vessel lumen 222 is greater than the pressure outside $P_o$ the blood vessel 226. This pressure difference, the flexibility of the plug 200, and its circumferential coverage and extension over the puncture 214 securely positions the plug 200 against the blood vessel wall 224 and around the puncture 214, even if the blood vessel wall 224 is irregular in shape. This is important to provide a tight and secure seal around the puncture 214 to prevent blood from oozing out of the blood vessel puncture 224 and/or tissue tract 226.

The pressure difference also causes the suture retrieval needles 202a, 202b to pierce the blood vessel wall 224 on each side of the puncture 214. The suture retrieval needles 202a, 202b may then be obtained with any retrieval device, such as a clamp. As illustrated in FIG. 6E, the suture retrieval needle 202a, 202b may be positioned on the pressure plug 200 such that the needles 202a, 202b expand and pierce the blood vessel wall 224 at an angle to ensure they will be received within the tissue tract 226. This will enable the user to easily retrieve the needles 202a, 202b out of the tissue tract 226. Once the needles 202a, 202b are withdrawn from the tissue tract 226, the cinching loop may be formed, cinched around the blood vessel puncture site, and released within the patient as described in detail above. Furthermore, a hemostasis pressure material may be used in combination with the pressure plug to provide an additional measure to plug the puncture 214 to ensure that blood will not flow out the puncture 214 or tissue tract 226.

FIG. 7 is a block diagram illustrating a method for releasing a cinching loop within a body. A first thread is removably joined to a second thread at 70 through a link formed from the second thread. The link may be located at the bottom half of the second thread. The link may be formed by folding the second thread in half to form a first half and a second half, by connecting the first tip to the second tip, by twisting the first half around the second half thereby forming a braid-like shape, or joining the first tip to the first half with a knot or any other means. The first thread may be removably joined to the second thread by inserting a first end of the first thread through the link and matching the first end with the second end of the first thread.

The first thread and second thread are positioned around a site to be secured at 72. The site may be a blood vessel puncture site, a site to hold two objects together, or a site to hold an object at a certain position or location. The top half of the second thread may then be connected to the first thread at 74 with a knot or by any other means to form the cinching loop.

The top half of the second thread and the knot may then be pushed toward the site and/or the first thread may be pulled away from the site at 76. The pushing and pulling of the first and second thread forms a tight cinching loop at the site location by causing the size and/or diameter of the cinching loop to decrease as it is cinched around the site. Once the cinching loop is secured around the site, the cinching loop may be released by withdrawing the first thread out of the body at 78. The first thread may be withdrawn by releasing the second end and pulling the first end out of the body.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. A method for releasing a tissue cinching loop within a cavity, comprising:
   providing a first thread having a first end, a second end, a first segment adjacent the first end, a second segment adjacent the second end, and a link joining the first segment and the second segment;
   providing a second thread having a first closed loop and a second closed loop
   inserting the first thread through the first closed loop in the second thread such that the first thread passes once and only once through the closed loop, thereby positioning the two segments of said first thread in a generally parallel arrangement, each segment being on an opposite side of said first closed loop in said second thread;
   pulling said first thread first end and second end through a first opening and a second opening within the cavity;
   joining said first thread to the second thread such that the first and second segments of the first thread pass through the second loop of the second thread to form a cinching loop;
   pulling said first thread first and second ends away from said cavity;
   thereby forming a tissue cinching loop in the second thread; and
   removing said first thread from said cavity thereby releasing said tissue cinching loop within said cavity.

2. The method of claim 1 wherein said inserting further comprises matching said first end with the second end of said first thread.

3. The method of claim 1 wherein said providing further comprises twisting a first half of said second thread around a second half of said second thread.

4. The method of claim 1 wherein said providing further comprises tying a knot to said second thread with a first end of said second thread.

5. The method of claim 1 wherein said first thread is made of a bioabsorbable material.

6. The method of claim 1 wherein said second thread is made of a bioabsorbable material.

7. The method of claim 1 wherein said removing further comprises withdrawing the first end of the first thread out of the cavity.

8. An apparatus to release a tissue cinching loop within a cavity, comprising:
   a first thread having a first end and a second end, a first segment adjacent the first end, a second segment adjacent the second end, and a link joining the first segment and the second segment, wherein the first and second segments are generally parallel;
   a second thread having a first closed loop comprising a first portion and a second portion, said portions being joined by a first link and a second link such that the first portion and the second portion are generally parallel; and
   a knot in the second thread, said knot forming a second closed loop of fixed dimension located adjacent to the second link of the second thread, said second closed loop being slidably disposed about the first portion and the second portion of the second thread;
   wherein the first thread passes once and only once between the first and second portions of the second thread and is disposed with the link of the first thread adjacent to the first link of the second thread such that the first thread first and second segments proximate the link of the first thread extend in a direction opposite the direction in which the first and second portions of the second thread leave the first link of the second thread.

9. The apparatus of claim 8, wherein withdrawing the first and second ends of the first thread in a direction away from the link in the first thread causes the knot in the second thread to slidably move from a first position about the first and second portions of the second thread to a second position nearer the second link.

10. The apparatus of claim 8, wherein withdrawing the first end of the first thread in a direction away from the link in the first thread results in the second end of the first thread passing through the first link in the second thread thereby releasing the second thread from the first thread.

11. The apparatus of claim 8, wherein the apparatus has an initial configuration in which the second closed loop formed by the knot in the second thread is slidably disposed about the first and second segments of the first thread rather than about the first and second portions of the second thread, further wherein withdrawing the first and second ends of the first thread in a direction away from the link in the first thread causes the second closed loop formed by the knot in the second thread to slide from the first and second segments of the first thread onto the first portion and second portions of the second thread.

12. The apparatus of claim 8, wherein the second thread is bioabsorbable.

13. The apparatus of claim 8, wherein the second thread is cinched around a blood vessel puncture site.

14. The apparatus of claim 8, wherein the second thread is cinched around at least one organ.

15. An apparatus to release a tissue cinching loop within a cavity, comprising:
   a first thread having a first end and a second end, a first segment adjacent the first end, a second segment adjacent the second end, and a link joining the first segment and the second segment, wherein the first and second segments are generally parallel;
   a second thread having a first end and a second end;
   a first knot in the second thread, said knot forming a first closed loop of fixed dimension located adjacent to the first end of the second thread; and
   a second knot in the second thread, said knot forming at least one second closed loop located adjacent to the second end of the second thread, said at least one second closed loop being slidably disposed about the second thread between the first and second knots;
   wherein the first thread passes once and only once through the first closed loop of the first knot of the second thread such that the first thread first segment and second segment proximate the link of the first thread extend in a direction opposite the direction in which the second thread leaves the first knot of the second thread.

16. The apparatus of claim 15, wherein withdrawing the first and second ends of the first thread in a direction away from the link in the first thread causes the second knot in the second thread to slidably move from a position about the second thread to a position nearer the second knot.

17. The apparatus of claim 15, wherein withdrawing the first end of the first thread in a direction away from the link in the first thread results in the second end of the first thread passing through the first knot in the second thread thereby releasing the second thread from the first thread.

18. The apparatus of claim 15, wherein the apparatus has an initial configuration in which the at least one closed loop formed by the second knot in the second thread is slidably disposed about first and second segments of the first thread rather than about the second thread between the first knot and the second knot, further wherein withdrawing the first and second ends of the first thread in a direction away from the link in the first thread causes the at least one closed loop formed by the second knot in the second thread to slide from the first and second segments of the first thread onto the second thread between the first and second knots.

19. The apparatus of claim 15, wherein the second thread is bioabsorbable.

20. The apparatus of claim 15, wherein the second thread is cinched around a blood vessel puncture site.

21. The apparatus of claim 15, wherein the second thread is cinched around at least one organ.

\* \* \* \* \*